United States Patent
Kuster et al.

(10) Patent No.: US 9,668,794 B2
(45) Date of Patent: Jun. 6, 2017

(54) PERIPROSTHETIC BONE PLATES

(71) Applicant: ZIMMER GMBH, Winterthur (CH)

(72) Inventors: Markus Kuster, Mosman Park (AU); Jordan Velikov, Horgen (CH); Simona Paganetto, Wintherthur (CH)

(73) Assignee: Zimmer GMBH, Winterthur (CH)

( * ) Notice: Subject to any disclaimer, the term of this patent is extended or adjusted under 35 U.S.C. 154(b) by 200 days.

(21) Appl. No.: 14/335,272

(22) Filed: Jul. 18, 2014

(65) Prior Publication Data

US 2014/0336713 A1    Nov. 13, 2014

Related U.S. Application Data

(63) Continuation of application No. 12/794,951, filed on Jun. 7, 2010, now Pat. No. 8,808,333.
(Continued)

(51) Int. Cl.
*A61B 17/80* (2006.01)
*A61B 17/74* (2006.01)
(Continued)

(52) U.S. Cl.
CPC .......... *A61B 17/8061* (2013.01); *A61B 17/74* (2013.01); *A61B 17/8042* (2013.01);
(Continued)

(58) Field of Classification Search
CPC ................................. A61B 17/8061
See application file for complete search history.

(56) References Cited

U.S. PATENT DOCUMENTS 2,406,832 A    9/1946   Hardinge
2,486,303 A    10/1949  Longfellow
(Continued)

FOREIGN PATENT DOCUMENTS

DE    8628766 U1    12/1986
EP    0515828 A1    12/1992
(Continued)

OTHER PUBLICATIONS

"U.S. Appl. No. 12/794,951, Response filed Oct. 9, 2012 to Non Final Office Action mailed Jul. 6, 2012", 17 pgs.
(Continued)

*Primary Examiner* — David Bates
*Assistant Examiner* — Olivia C Chang
(74) *Attorney, Agent, or Firm* — Schwegman, Lundberg & Woessner, P.A.

(57) ABSTRACT

The present disclosure relates to bone plates that are configured for use with bones having periprosthetic fractures. For example, in the event that a proximal femur is fractured in an area that is adjacent to a prosthetic component, such as a femoral stem used in a hip replacement, the periprosthetic bone plates of the present invention may be used. In one exemplary embodiment, the periprosthetic bone plates include a periprosthetic zone having a plurality of central apertures and a plurality of outer apertures that are offset from the central apertures. The periprosthetic zone may further include a plurality of indentations, each indentation extending longitudinally between adjacent outer apertures to narrow a width of the bone plate.

18 Claims, 9 Drawing Sheets

Related U.S. Application Data

(60) Provisional application No. 61/223,318, filed on Jul. 6, 2009.

(51) Int. Cl.
    A61B 17/82 (2006.01)
    A61B 17/86 (2006.01)
    A61F 2/30 (2006.01)
    A61F 2/36 (2006.01)

(52) U.S. Cl.
    CPC ........... *A61B 17/8085* (2013.01); *A61B 17/82* (2013.01); *A61B 17/86* (2013.01); *A61B 17/8665* (2013.01); *A61F 2/30739* (2013.01); *A61F 2/36* (2013.01)

(56) References Cited

U.S. PATENT DOCUMENTS

| | | |
|---|---|---|
| 3,547,114 A | 12/1970 | Haboush |
| 3,659,595 A | 5/1972 | Haboush |
| 3,782,374 A | 1/1974 | Fischer |
| 4,364,382 A | 12/1982 | Mennen |
| 4,438,762 A | 3/1984 | Kyle |
| 4,573,458 A | 3/1986 | Lower |
| 4,776,330 A | 10/1988 | Chapman et al. |
| 4,838,252 A | 6/1989 | Klaue |
| 4,867,144 A | 9/1989 | Karas et al. |
| 4,903,691 A | 2/1990 | Heinl |
| 4,905,679 A | 3/1990 | Morgan |
| 4,973,332 A | 11/1990 | Kummer |
| 4,988,350 A | 1/1991 | Herzberg |
| 5,002,544 A | 3/1991 | Klaue et al. |
| 5,006,120 A | 4/1991 | Carter |
| 5,015,248 A | 5/1991 | Burstein et al. |
| 5,041,114 A | 8/1991 | Chapman et al. |
| 5,053,036 A | 10/1991 | Perren et al. |
| 5,151,103 A | 9/1992 | Tepic et al. |
| 5,190,544 A | 3/1993 | Chapman et al. |
| 5,330,477 A | 7/1994 | Crook |
| 5,364,398 A | 11/1994 | Chapman et al. |
| 5,462,547 A | 10/1995 | Weigum |
| 5,484,439 A | 1/1996 | Olson et al. |
| 5,601,553 A | 2/1997 | Trebing et al. |
| 5,709,686 A | 1/1998 | Talos et al. |
| 5,718,705 A | 2/1998 | Sammarco |
| 5,728,099 A | 3/1998 | Tellman et al. |
| 5,772,662 A | 6/1998 | Chapman et al. |
| 5,807,396 A | 9/1998 | Raveh |
| 5,810,823 A | 9/1998 | Klaue et al. |
| 5,827,286 A | 10/1998 | Incavo et al. |
| D402,032 S | 12/1998 | Stone |
| 5,904,683 A | 5/1999 | Pohndorf et al. |
| 5,938,664 A | 8/1999 | Winquist et al. |
| 5,964,763 A | 10/1999 | Incavo et al. |
| 5,973,223 A | 10/1999 | Tellman et al. |
| 6,007,538 A | 12/1999 | Levin |
| 6,096,040 A | 8/2000 | Esser |
| 6,217,580 B1 | 4/2001 | Levin |
| D443,060 S | 5/2001 | Benirschke et al. |
| 6,283,969 B1 | 9/2001 | Grusin et al. |
| 6,306,136 B1 | 10/2001 | Baccelli |
| 6,309,393 B1 | 10/2001 | Tepic et al. |
| 6,348,052 B1 | 2/2002 | Sammarco |
| 6,364,882 B1 | 4/2002 | Orbay |
| D458,374 S | 6/2002 | Bryant et al. |
| D458,683 S | 6/2002 | Bryant et al. |
| D458,684 S | 6/2002 | Bryant et al. |
| D458,996 S | 6/2002 | Bryant et al. |
| 6,402,756 B1 | 6/2002 | Ralph et al. |
| D463,557 S | 9/2002 | Bryant et al. |
| D463,558 S | 9/2002 | Bryant et al. |
| D463,559 S | 9/2002 | Bryant et al. |
| 6,454,770 B1 | 9/2002 | Klaue |
| D464,136 S | 10/2002 | Bryant et al. |
| D464,731 S | 10/2002 | Bryant et al. |
| D469,532 S | 1/2003 | Bryant et al. |
| D469,533 S | 1/2003 | Bryant et al. |
| D469,534 S | 1/2003 | Bryant et al. |
| 6,506,191 B1 | 1/2003 | Joos |
| D469,874 S | 2/2003 | Bryant et al. |
| D469,875 S | 2/2003 | Bryant et al. |
| D470,588 S | 2/2003 | Bryant et al. |
| 6,595,993 B2 | 7/2003 | Donno et al. |
| D479,331 S | 9/2003 | Pike et al. |
| 6,623,486 B1 | 9/2003 | Weaver et al. |
| 6,645,208 B2 | 11/2003 | Apfelbaum et al. |
| 6,666,867 B2 | 12/2003 | Ralph et al. |
| 6,689,134 B2 | 2/2004 | Ralph et al. |
| 6,712,820 B2 | 3/2004 | Orbay |
| 6,755,832 B2 | 6/2004 | Happonen et al. |
| 6,786,909 B1 | 9/2004 | Dransfield et al. |
| 6,821,278 B2 | 11/2004 | Frigg et al. |
| 6,852,113 B2 | 2/2005 | Nathanson et al. |
| 6,866,665 B2 | 3/2005 | Orbay |
| D505,205 S | 5/2005 | Freid |
| 6,890,335 B2 | 5/2005 | Grabowski et al. |
| D520,637 S | 5/2006 | Kay et al. |
| 7,041,105 B2 | 5/2006 | Michelson |
| 7,044,952 B2 | 5/2006 | Michelson |
| 7,052,499 B2 | 5/2006 | Steger et al. |
| 7,090,676 B2 | 8/2006 | Huebner et al. |
| 7,097,645 B2 | 8/2006 | Michelson |
| 7,112,202 B2 | 9/2006 | Michelson |
| 7,115,130 B2 | 10/2006 | Michelson |
| 7,118,573 B2 | 10/2006 | Michelson |
| 7,128,744 B2 | 10/2006 | Weaver et al. |
| 7,156,847 B2 | 1/2007 | Abramson |
| 7,169,150 B2 | 1/2007 | Shipp et al. |
| D536,453 S | 2/2007 | Young et al. |
| 7,186,256 B2 | 3/2007 | Michelson |
| 7,303,564 B2 | 12/2007 | Freid et al. |
| 7,318,825 B2 | 1/2008 | Butler et al. |
| 7,326,212 B2 | 2/2008 | Huebner |
| 7,341,589 B2 | 3/2008 | Weaver et al. |
| 7,399,301 B2 | 7/2008 | Michelson |
| D576,731 S | 9/2008 | Strnad et al. |
| D580,056 S | 11/2008 | Orthner |
| D580,057 S | 11/2008 | Ramadani |
| 7,479,143 B2 | 1/2009 | Suh |
| 7,547,306 B2 | 6/2009 | Michelson |
| 7,621,943 B2 | 11/2009 | Michelson |
| 7,695,473 B2 | 4/2010 | Ralph et al. |
| 7,704,250 B2 | 4/2010 | Michelson |
| 7,704,251 B2 | 4/2010 | Huebner et al. |
| 7,727,265 B2 | 6/2010 | Paul |
| 7,740,630 B2 | 6/2010 | Michelson |
| 7,803,157 B2 | 9/2010 | Michelson |
| 7,811,285 B2 | 10/2010 | Michelson |
| 7,824,432 B2 | 11/2010 | Michelson |
| 7,985,224 B2 | 7/2011 | Michelson |
| 8,808,333 B2 | 8/2014 | Kuster et al. |
| 2002/0188296 A1 | 12/2002 | Michelson |
| 2003/0055429 A1 | 3/2003 | Ip |
| 2004/0019353 A1 | 1/2004 | Freid et al. |
| 2004/0092939 A1 | 5/2004 | Freid et al. |
| 2004/0097937 A1 | 5/2004 | Pike et al. |
| 2004/0102775 A1 | 5/2004 | Huebner |
| 2004/0102778 A1 | 5/2004 | Huebner et al. |
| 2004/0116930 A1 | 6/2004 | O'Driscoll et al. |
| 2004/0116931 A1 | 6/2004 | Carlson |
| 2004/0153073 A1 | 8/2004 | Orbay |
| 2004/0210223 A1 | 10/2004 | Pisharodi |
| 2004/0220572 A1 | 11/2004 | Michelson |
| 2005/0049595 A1 | 3/2005 | Suh et al. |
| 2005/0090825 A1 | 4/2005 | Pfefferle et al. |
| 2005/0234458 A1 | 10/2005 | Huebner |
| 2006/0089648 A1 | 4/2006 | Masini |
| 2006/0100625 A1 | 5/2006 | Ralph et al. |
| 2006/0173458 A1 | 8/2006 | Forstein et al. |
| 2006/0200134 A1 | 9/2006 | Freid et al. |
| 2006/0217722 A1 | 9/2006 | Dutoit et al. |
| 2006/0229619 A1 | 10/2006 | Orbay et al. |
| 2006/0235402 A1 | 10/2006 | Celli et al. |

(56) References Cited

U.S. PATENT DOCUMENTS

| | | |
|---|---|---|
| 2006/0235404 A1 | 10/2006 | Orbay et al. |
| 2006/0241607 A1 | 10/2006 | Myerson et al. |
| 2006/0247627 A1 | 11/2006 | Farris |
| 2007/0055253 A1 | 3/2007 | Orbay et al. |
| 2007/0239163 A1 | 10/2007 | Strnad et al. |
| 2007/0293864 A1 | 12/2007 | Reimels et al. |
| 2008/0015589 A1 | 1/2008 | Hack |
| 2008/0021477 A1 | 1/2008 | Strnad et al. |
| 2008/0065070 A1 | 3/2008 | Freid et al. |
| 2008/0086137 A1 | 4/2008 | Probe |
| 2008/0132960 A1 | 6/2008 | Weaver et al. |
| 2008/0200955 A1 | 8/2008 | Tepic |
| 2008/0234676 A1 | 9/2008 | Schulze et al. |
| 2008/0300637 A1 | 12/2008 | Austin et al. |
| 2009/0018587 A1 | 1/2009 | Bottlang |
| 2009/0018588 A1 | 1/2009 | Eckhof et al. |
| 2009/0076509 A1 | 3/2009 | Bush, Jr. et al. |
| 2009/0105717 A1* | 4/2009 | Bluechel ............ A61B 17/8061 606/280 |
| 2009/0275947 A1 | 11/2009 | Graham et al. |
| 2009/0299370 A1 | 12/2009 | Kiester |
| 2009/0318920 A1 | 12/2009 | Jacobs |
| 2010/0010541 A1 | 1/2010 | Boomer et al. |
| 2010/0016858 A1 | 1/2010 | Michel |
| 2010/0121328 A1 | 5/2010 | Reitzig et al. |
| 2010/0137868 A1 | 6/2010 | Orbay et al. |
| 2010/0234896 A1 | 9/2010 | Lorenz et al. |
| 2010/0274248 A1 | 10/2010 | Overes et al. |
| 2010/0324559 A1 | 12/2010 | Ralph et al. |
| 2011/0004252 A1 | 1/2011 | Velikov |
| 2011/0022049 A1 | 1/2011 | Huebner et al. |
| 2011/0054528 A1 | 3/2011 | Michelson |
| 2011/0137314 A1 | 6/2011 | Kuster et al. |

FOREIGN PATENT DOCUMENTS

| | | |
|---|---|---|
| EP | 0934731 A1 | 8/1999 |
| EP | 1477124 A1 | 11/2004 |
| FR | 2405062 A1 | 5/1979 |
| FR | 2405706 A1 | 5/1979 |
| GB | 1517161 A | 7/1978 |
| GB | 2158716 A | 11/1985 |
| GB | 2331244 A | 5/1999 |
| JP | 11299804 A | 11/1999 |
| WO | WO-9306789 A2 | 4/1993 |
| WO | WO-9938447 A1 | 8/1999 |
| WO | WO-9938448 A1 | 8/1999 |
| WO | WO-0130251 A1 | 5/2001 |
| WO | WO-2004045389 A2 | 6/2004 |
| WO | WO-2004089233 A1 | 10/2004 |
| WO | WO-2007006430 A1 | 1/2007 |
| WO | WO-2007137437 A2 | 12/2007 |
| WO | WO-2008019511 A1 | 2/2008 |
| WO | WO-2008075160 A1 | 6/2008 |
| WO | WO-200809242 A1 | 8/2008 |
| WO | WO-2009009521 A2 | 1/2009 |
| WO | WO-2011003494 A1 | 1/2011 |
| WO | WO-2011086524 A1 | 7/2011 |

OTHER PUBLICATIONS

"U.S. Appl. No. 12/794,951, Advisory Action mailed Mar. 7, 2013", 3 pgs.

"U.S. Appl. No. 12/794,951, Examiner Interview Summary mailed Jan. 30, 2013", 3 pgs.

"U.S. Appl. No. 12/794,951, Examiner Interview Summary mailed Oct. 12, 2012", 6 pgs.

"U.S. Appl. No. 12/794,951, Final Office Action mailed Jan. 4, 2013", 8 pgs.

"U.S. Appl. No. 12/794,951, Non Final Office Action mailed Jul. 6, 2012", 7 pgs.

"U.S. Appl. No. 12/794,951, Notice of Allowance mailed Apr. 11, 2014", 7 pgs.

"U.S. Appl. No. 12/794,951, Response filed Feb. 20, 2013 to Final Office Action mailed Jan. 4, 2013", 14 pgs.

"U.S. Appl. No. 12/794,951, Response filed May 8, 2012 to Restriction Requirement mailed Apr. 11, 2012", 10 pgs.

"U.S. Appl. No. 12/794,951, Restriction Requirement mailed Apr. 11, 2012", 6 pgs.

"DHS/DCS System. Including LCP DHS and DHS Blade", Synthes, Technique Guide, (2007), 48 pgs.

"International Application Serial No. PCT/EP2010/003433, Written Opinion mailed Nov. 8, 2010", 6 pgs.

"International Application Serial No. PCT/EP2010/003433, International Preliminary Report on Patentability mailed Jun. 17, 2011", 13 pgs.

"International Application Serial No. PCT/EP2010/003433, International Search Report mailed on Nov. 8, 2010", 5 pgs.

"LCP Distal Femur Plates", Synthes USA Brochure, (2007), 7 pgs.

"Locking Attachment Plate. For Treatment of Periprosthetic Fractures", Synthes, Technique Guide, (2009), 28 pgs.

"Locking Compression Plate (LCP) System", Synthes USA Brochure, (2003), 6 pgs.

"Periprosthetics", Intrauma S.r.l, Italy Brochure, (2009,2010), 8 pgs.

"Trochanter Stabilization Plate for DHS", Synthes USA, Technique Guide, (2000), 11 pgs.

"Universal Locking Trochanter Stabilization Plate (ULTSP). For Use with the DHS/DCS and LCP DHHS Systems.", Synthes Inc., Technique Guide, (2007), 17 pgs.

"Zimmer NCB Distal Femoral Plating System, The Right Locking Option for Tough Fractures", Surgical Technique, (2006), 28 pgs.

"Zimmer NCB Plating System, A Locking Plate System That Expands a Surgeon's Options in Trauma Surgery", Product Brochure, Zimmer,Inc, 97-2370-001-00 5 ML, (2006), 6 pgs.

Lefevre, C, et al., "La Plaque Femorale Anatomique: Une Solution Brestoise Pour Le Traitement Des Fractures Diaphysaires Sur Implants Intramedullaires", [Online]. Retrieved from the Internet: <http://www.maitrise-orthop.com/viewPage.do?id+786>, (accessd Apr. 14, 2010), 9 pgs.

* cited by examiner

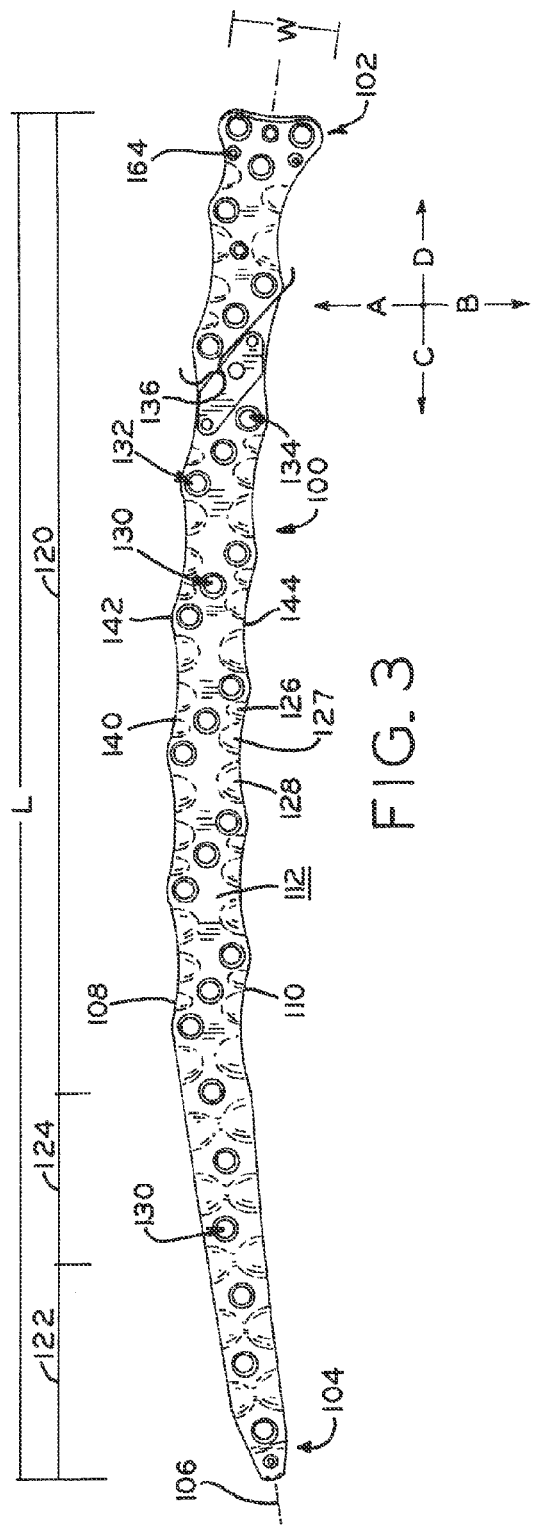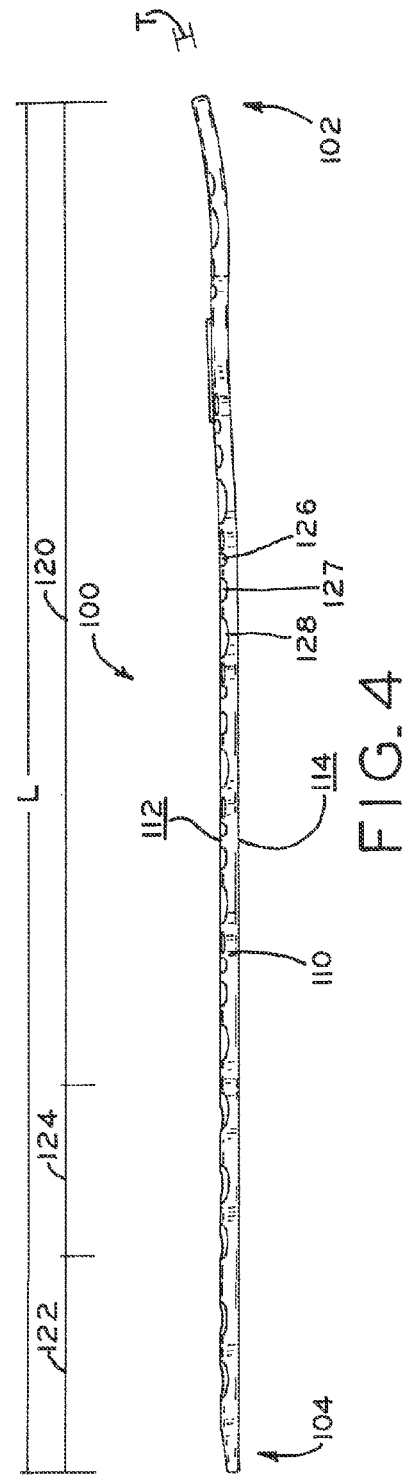
FIG. 3
FIG. 4

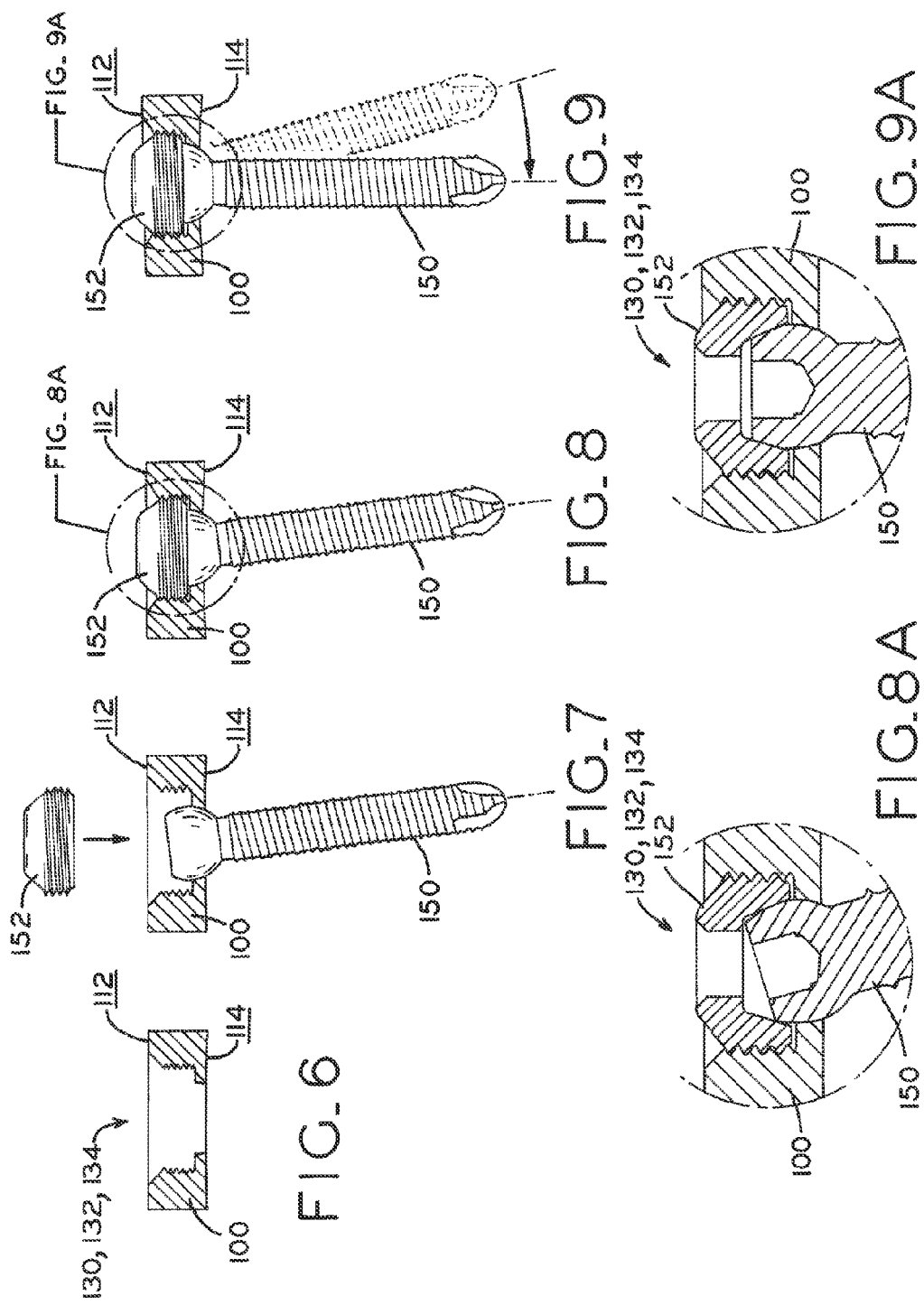

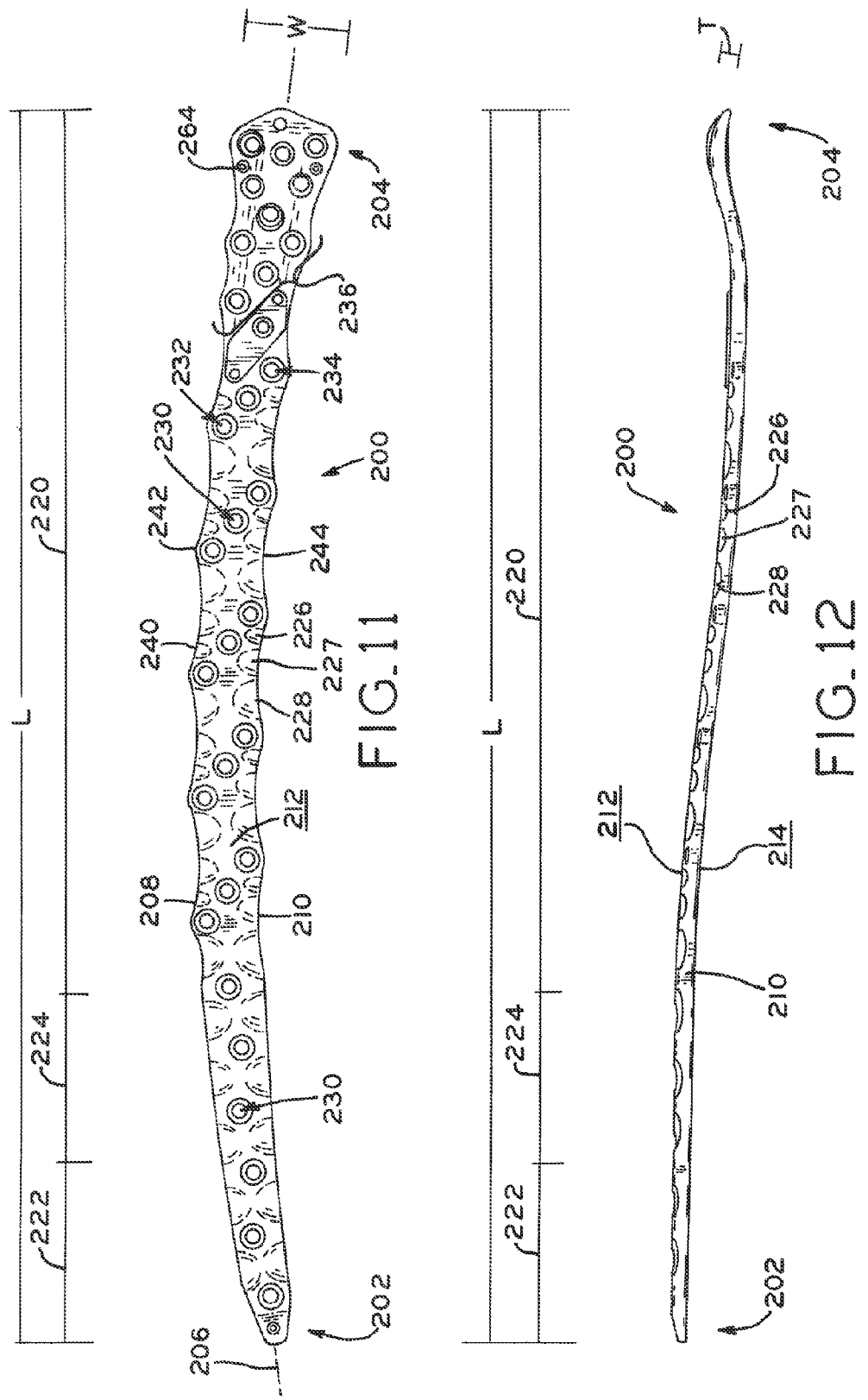

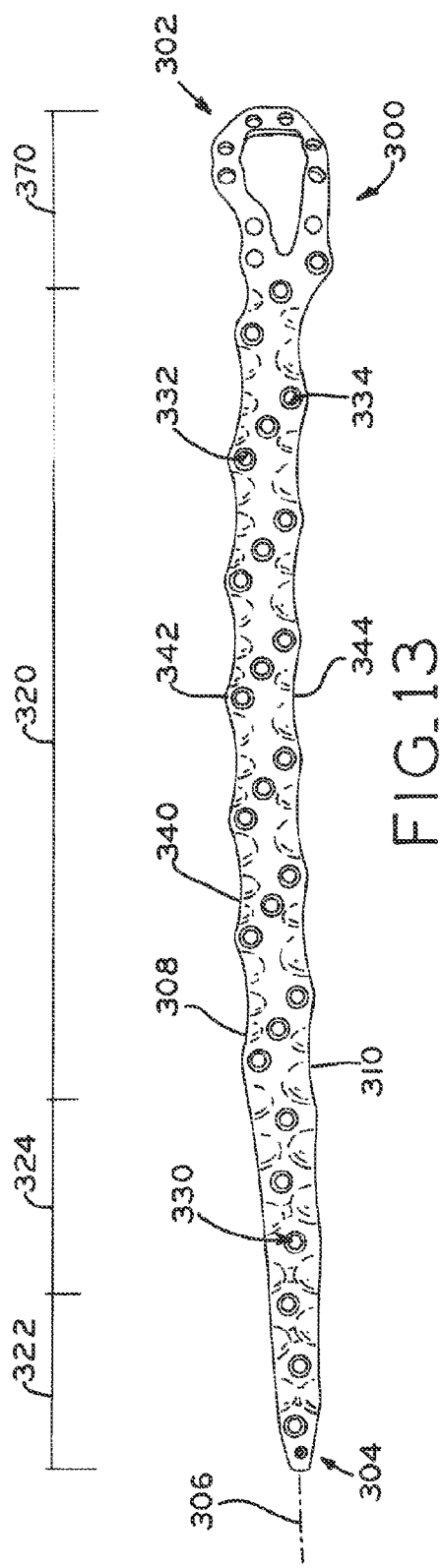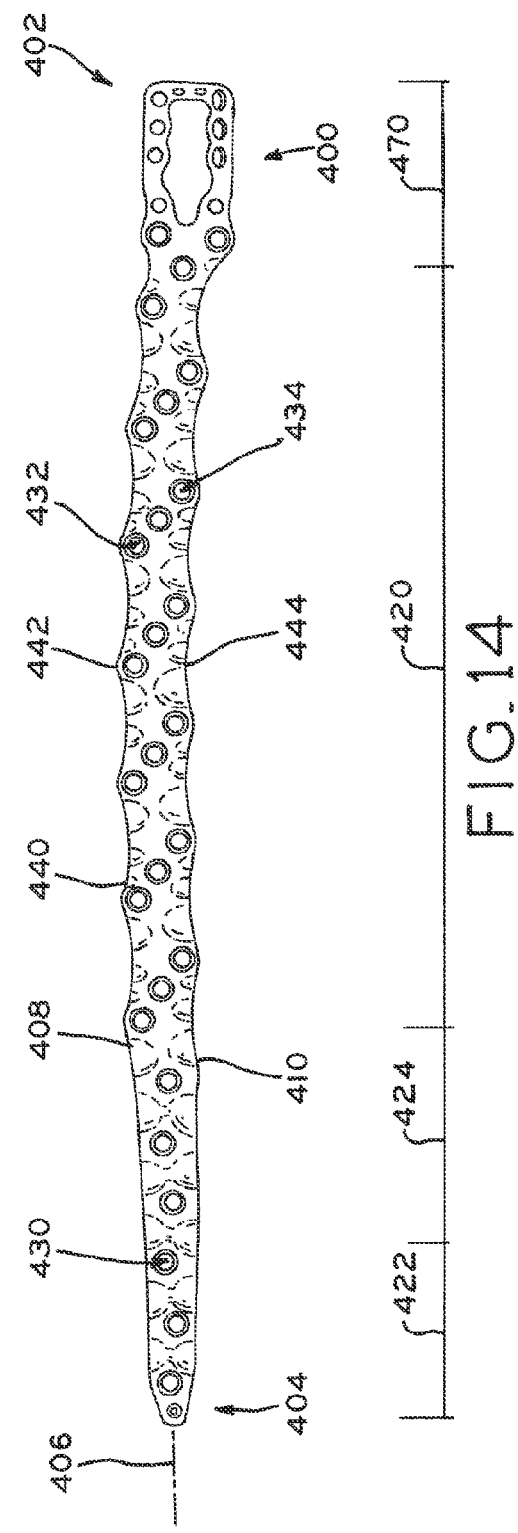

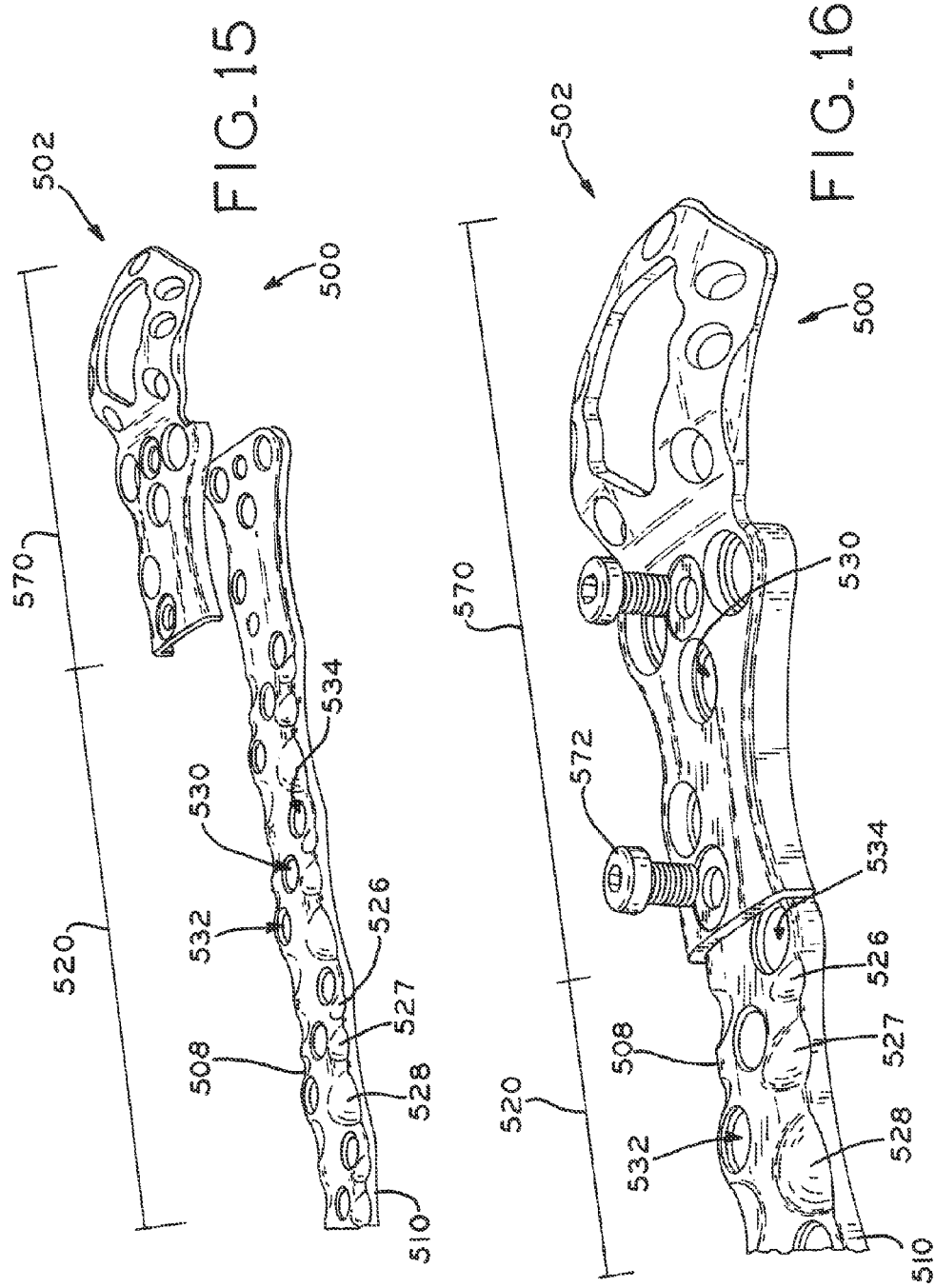

PERIPROSTHETIC BONE PLATES

CROSS-REFERENCE TO RELATED APPLICATIONS

This application is a continuation of U.S. application Ser. No. 12/794,951, filed Jun. 7, 2010, now issued as U.S. Pat. No. 8,808,333, which claims priority from U.S. Provisional Patent Application Ser. No. 61/223,318, entitled "Periprosthetic Bone Plates," filed Jul. 6, 2009, the disclosure of which is hereby expressly incorporated by reference herein in its entirety.

BACKGROUND

1. Field of the Invention

The present invention relates to bone plates, and more particularly, to periprosthetic bone plates and methods for implanting the same.

2. Description of the Related Art

Bone plates are commonly used to secure adjacent sections of a fractured bone together and to facilitate healing of the fractured bone. Such bone plates may be attached to the fractured bone using a plurality of bone screws. For example, a surgeon may position a bone plate to extend across a fracture line, and then the surgeon may secure the bone plate in place by inserting a plurality of bone screws through apertures in the bone plate and into the patient's bone. However, when fractures of the bone occur in areas adjacent to a prosthetic implant, such as a femoral stem, the prosthetic implant may block areas of the patient's bone intended for the bone screws.

Periprosthetic bone plates are available for stabilizing a fracture in an area adjacent to a prosthetic implant. Such bone plates may include offset apertures for guiding bone screws into the bone. However, known periprosthetic bone plates suffer from certain disadvantages. First, known periprosthetic bone plates may be configured to direct unicortical bone screws into areas of the bone adjacent to the prosthetic implant to avoid the prosthetic implant. Although unicortical bone screws may stop short of the prosthetic implant to avoid interfering with and/or damaging the prosthetic implant, unicortical screw anchorage is not as strong as cancellous or bicortical screw anchorage, for example. Also, to accomplish a sufficient offset, known periprosthetic bone plates may include flanges that protrude from the bone plate, with the offset apertures extending through these flanges. However, the flanges may catch onto and strip the patient's muscle tissue while the bone plate is being implanted.

SUMMARY

The present invention provides bone plates that are configured for use with bones having periprosthetic fractures. For example, in the event that a proximal femur is fractured in an area that is adjacent to a prosthetic component, such as a femoral stem used in a hip replacement, the periprosthetic bone plates of the present invention may be used to accommodate the prosthetic component. In one exemplary embodiment, the periprosthetic bone plates include a periprosthetic zone having a plurality of central apertures and a plurality of outer apertures that are offset from the central apertures. The periprosthetic zone may further include a plurality of indentations, each indentation extending longitudinally between adjacent outer apertures to narrow a width of the bone plate.

According to an exemplary embodiment of the present invention, a bone plate is provided for use with a bone having a periprosthetic fracture. The bone plate has a longitudinal axis that extends from a first end to a second end of the bone plate. The bone plate includes: a bottom surface configured to face the bone; a top surface opposite the bottom surface; a first side wall and a second side wall joining the top and bottom surfaces; and a periprosthetic zone located at the first end of the bone plate. The periprosthetic zone includes a plurality of outer apertures that extend through the bone plate from the top surface to the bottom surface, the plurality of outer apertures offset from the longitudinal axis in a direction perpendicular to the longitudinal axis, the first and second side walls undulating in the periprosthetic zone such that, along a first length of the bone plate and in a direction from the first end toward the second end of the bone plate, the first side wall narrows inwardly toward the longitudinal axis as the second side wall widens outwardly from the longitudinal axis, and along a second length of the bone plate in the direction from the first end toward the second end of the bone plate, the first side wall widens outwardly from the longitudinal axis as the second side wall narrows inwardly toward the longitudinal axis.

According to another exemplary embodiment of the present invention, a bone plate is provided for use with a bone having a periprosthetic fracture. The bone plate has a longitudinal axis that extends from a first end to a second end of the bone plate. The bone plate includes: a planar bottom surface configured to face the bone; a top surface opposite the bottom surface; a plurality of side walls joining the top and bottom surfaces; a plurality of outer apertures that extend through the bone plate from the top surface to the bottom surface, the plurality of outer apertures offset from the longitudinal axis in a direction perpendicular to the longitudinal axis; and a plurality of indentations in the side walls, each indentation extending longitudinally between adjacent outer apertures to narrow the bone plate in a direction perpendicular to the longitudinal axis of the bone plate.

According to yet another exemplary embodiment of the present invention, a method is provided for repairing a bone having a periprosthetic fracture, the bone including a prosthetic component implanted therein. The method includes the step of providing a bone plate having a longitudinal axis that extends from a first end to a second end, the bone plate including a periprosthetic zone located at the first end of the bone plate, the periprosthetic zone including a plurality of outer apertures offset from the longitudinal axis in a direction perpendicular to the longitudinal axis, the plurality of outer apertures extending through the bone plate substantially in parallel, the bone plate narrowing inwardly toward the longitudinal axis between adjacent outer apertures. The method also includes the step of securing the bone plate onto the bone by inserting a bone screw into one of the plurality of outer apertures while avoiding the prosthetic component.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 3 is a top plan view of the bone plate of FIG. 1;

FIG. 4 is an elevational view of the bone plate of FIG. 1;

FIG. 6 is a cross-sectional view of a portion of the bone plate of FIG. 1 showing an aperture in the bone plate;

FIG. 7 is a view similar to FIG. 6 showing a bone screw in the aperture of the bone plate and a locking cap;

FIG. 8 is a view similar to FIG. 7 showing the locking cap in the aperture of the bone plate, the locking cap securing the bone screw in an angled arrangement;

FIG. 8A is a cross-sectional view of the encircled portion of FIG. 8;

FIG. 9 is a view similar to FIG. 8 showing the locking cap in the aperture of the bone plate, the locking cap securing the bone screw in a perpendicular arrangement;

FIG. 9A is a cross-sectional view of the encircled portion of FIG. 9;

FIG. 11 is a top plan view of the bone plate of FIG. 10;

FIG. 12 is an elevational view of the bone plate of FIG. 10;

FIG. 13 is a top plan view of yet another exemplary bone plate of the present invention;

FIG. 14 is a top plan view of still yet another exemplary bone plate of the present invention;

FIG. 15 is a perspective view of a portion of still yet another exemplary bone plate of the present invention having a modular trochanteric zone detached from the bone plate; and FIG. 16 is a perspective view of a portion of the bone plate of FIG. 15, showing the modular trochanteric zone attached to the bone plate.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
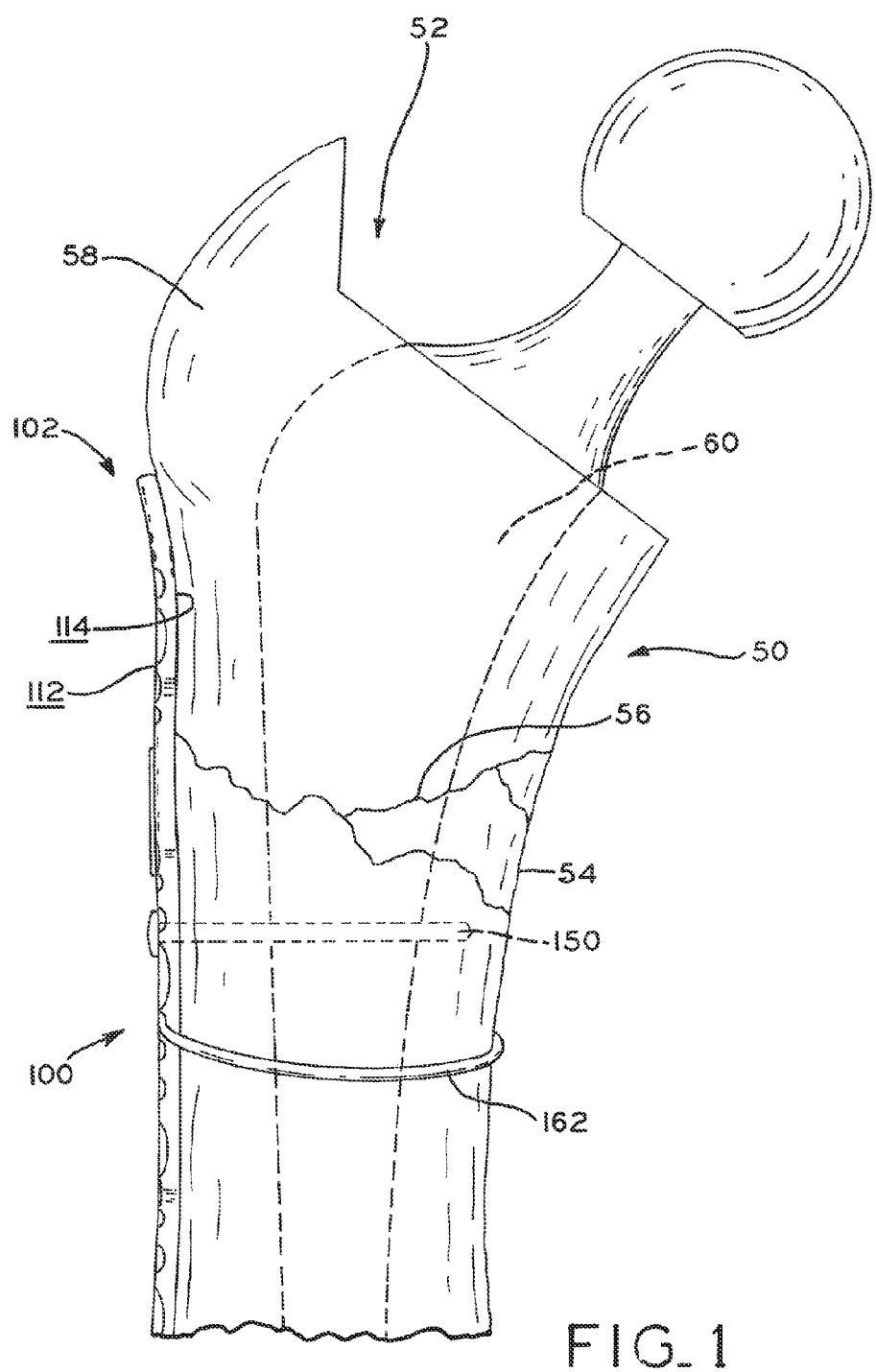
FIG. 1 is an elevational view of a portion of an exemplary bone plate of the present invention secured onto a fractured proximal femur, the femur having a femoral hip stem implanted therein.

FIG. 1 depicts a patient's proximal femur 50 having proximal end 52, a distal end (not shown), and shaft 54 extending therebetween. Shaft 54 of femur 50 includes fracture 56. In the illustrated embodiment, a prosthetic component, specifically femoral stem 60 of a hip replacement system, is implanted into the patient's proximal femur 50. As shown in FIG. 1, fracture 56 in femur 50 is located adjacent to femoral stem 60.

As shown in FIG. 1, bone plate 100 is secured onto shaft 54 of femur 50 to extend across fracture 56. Although bone plate 100 is described and depicted herein as being secured onto a patient's femur 50, bone plate 100 may be sized for securement onto a patient's tibia, fibula, humerus, radius, ulna, or another long bone.

Figure 2:
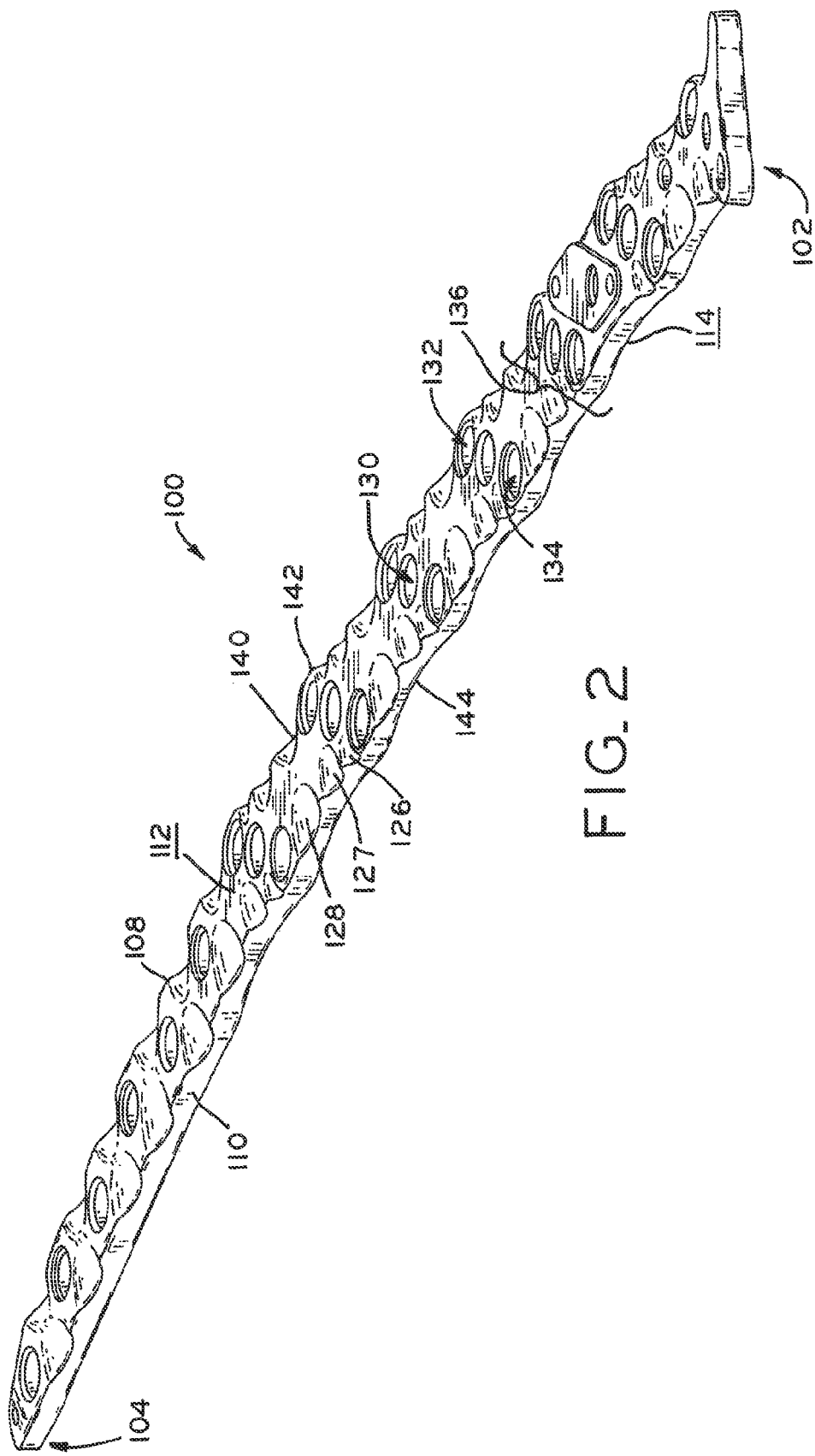
FIG. 2 is a perspective view of the bone plate of FIG. 1.

Referring to FIGS. 2-4, bone plate 100 of the present invention is provided for use on proximal end 52 of femur 50. Bone plate 100 is configured for use on a patient's left leg, although a mirror image plate may be provided for use on a patient's right leg. Bone plate 100 includes proximal end 102 and distal end 104. Proximal end 102 of bone plate 100 is configured to rest against proximal end 52 of femur 50, with bone plate 100 extending distally along shaft 54 of femur 50 and across fracture 56 (FIG. 1). Bone plate 100 also includes longitudinal axis 106 and side walls 108, 110, that extend from proximal end 102 to distal end 104 of bone plate 100. Rather than being a straight line, longitudinal axis 106 of bone plate 100 may have a slight bend to accommodate the shape of the patient's bone.

Bone plate 100 further includes a first, exposed surface 112 and a second, bone-facing surface 114 that span between side walls 108, 110. According to an exemplary embodiment of the present invention, and as shown in FIGS. 2 and 4, surfaces 112, 114, of bone plate 100 are generally planar to facilitate smooth insertion of the bone plate 100 beneath muscle tissue of the patient. For example, as disclosed in co-pending U.S. patent application Ser. No. 12/683,962, entitled "A Plate for the Treatment of Bone Fractures," filed Jan. 7, 2010, the disclosure of which is expressly incorporated by reference herein in its entirety, exposed surface 112 of bone plate 100 may have a central planar region near longitudinal axis 106 in a cross-section perpendicular to longitudinal axis 106, and bone-facing surface 114 of bone plate 100 may have outer planar regions near side walls 108, 110, in the same cross-section perpendicular to longitudinal axis 106. It is within the scope of the present invention that surfaces 112, 114, of bone plate 100 may be contoured to the shape of femur 50 (FIG. 1). For example, as disclosed in the above-incorporated U.S. patent application Ser. No. 12/683, 962, bone-facing surface 114 of bone plate 100 may include a concave region between the outer planar regions that is configured to wrap around femur 50.

To accommodate bones of different sizes, bone plate 100 may be provided in various sizes. For example, bone plate 100 may vary in length L along longitudinal axis 106 from approximately 245 mm to approximately 401 mm. According to an exemplary embodiment of the present invention, a set of bone plates 100 may be provided in lengths of 245 mm, 285 mm, 324 mm, 363 mm, and 401 mm, for example.

Bone plate 100 includes periprosthetic zone 120, non-periprosthetic zone 122, and transition zone 124 located between periprosthetic zone 120 and non-periprosthetic zone 122. As shown in FIG. 3, periprosthetic zone 120 is located near proximal end 102 of bone plate 100 and non-periprosthetic zone 122 is located near distal end 104 of bone plate 100.

Bone plate 100 may progressively decrease in width W (between side walls 108, 110) from periprosthetic zone 120, to transition zone 124, to non-periprosthetic zone 122, as shown in FIG. 3. For example, bone plate 100 may be about 25 mm wide in periprosthetic zone 120, about 16 mm wide in transition zone 124, and about 14.5 mm wide in non-periprosthetic zone 122.

Also, bone plate 100 may vary in thickness T (between exposed surface 112 and bone-facing surface 114) across periprosthetic zone 120, transition zone 124, and non-periprosthetic zone 122, as shown in FIG. 4. In an exemplary embodiment, the thickness T of bone plate 100 may be greatest in transition zone 124, with the thickness T of bone plate 100 decreasing in both periprosthetic zone 120 and non-periprosthetic zone 122. For example, bone plate 100 may be about 5 mm thick in periprosthetic zone 120, about 5.7 mm thick in transition zone 124, and about 4.8 mm thick in non-periprosthetic zone 122. Due to the varied thickness T of bone plate 100, the strength of bone plate 100 may vary across its length L. For example, transition zone 124 of bone plate 100 may be stronger than periprosthetic zone 120 and/or non-periprosthetic zone 122 of bone plate 100.

As shown in FIG. 3, exposed surface 112 of bone plate 100 includes a plurality of concave scallops 126, 127, 128, of various sizes. Scallops 126, 127, 128, are arranged along side walls 108, 110, of bone plate 100 to narrow the thickness T (FIG. 4) of bone plate 100 and to control the mechanical resistance of bone plate 100. For example, bone plate 100 may be configured to bend along large scallops 128 to a greater extent than along small scallops 126. Each scallop 126, 127, 128, may have a maximum depth along its corresponding side wall 108, 110, of bone plate 100, with each scallop 126, 127, 128, gradually decreasing in depth inwardly toward longitudinal axis 106 of bone plate 100, as shown in FIG. 2.

Within periprosthetic zone 120, bone plate 100 includes a plurality of central apertures 130 that are generally aligned along longitudinal axis 106 of bone plate 100, as shown in FIG. 3. Bone plate 100 also includes a plurality of outer apertures 132, 134, positioned alongside central apertures 130.

As shown in FIG. 3, outer apertures 132, 134, are horizontally offset (e.g., medially/laterally offset, anteriorly/posteriorly offset) from central apertures 130. For example, in the illustrated embodiment of FIG. 3, outer apertures 132 are horizontally offset from adjacent central apertures 130 in the direction of arrow A, and outer apertures 134 are horizontally offset from adjacent central apertures 130 in the direction of arrow B. The center of each outer aperture 132, 134, may be horizontally offset from the center of the adjacent central aperture 130 by approximately 5 mm, 6 mm, 7 mm, 8 mm, 9 mm, 10 mm, or more. In an exemplary embodiment, the center of each outer aperture 132, 134, is horizontally offset from the center of the adjacent central aperture 130 by approximately 7.5 mm, such that the centers of outer apertures 132, 134, are horizontally offset from one another by approximately 13 mm. In certain embodiments, outer apertures 132 may be arranged in a first row that is generally parallel to central apertures 130, and outer apertures 134 may be arranged in a second row that is also generally parallel to central apertures 130.

Also, as shown in FIG. 3, outer apertures 132, 134 are vertically offset (e.g., proximally/distally offset) from central apertures 130 and each other. For example, in the illustrated embodiment of FIG. 3, outer apertures 132 are vertically offset from adjacent central apertures 130 in the direction of arrow C, and outer apertures 134 are vertically offset from adjacent central apertures 130 in the direction of arrow D. The center of each outer aperture 132, 134, may be vertically offset from the center of the adjacent central aperture 130 by approximately 5 mm, 6 mm, 7 mm, 8 mm, 9 mm, 10 mm, or more. By vertically offsetting outer apertures 132, 134, from central apertures 130 along arrows C, D, the width W of bone plate 100 may be reduced. If central apertures 130 and outer apertures 132, 134, were all aligned in a direction perpendicular to longitudinal axis 106, on the other hand, bone plate 100 would have to be sufficiently wide in this perpendicular direction to accommodate all three apertures 130, 132, 134.

According to an exemplary embodiment of the present invention, three apertures 130, 132, 134, may be organized in a subset 136 that extends diagonally across bone plate 100, as shown in FIG. 3. Bone plate 100 may include a plurality of spaced-apart subsets 136 across its length. In certain embodiments, the entire subset 136 of apertures 130, 132, 134, is vertically offset (e.g., proximally/distally offset) from the adjacent subset 136. Large scallops 128 may extend between adjacent subsets 136, with small scallops 126 and medium scallops 127 extending into each subset 136, as shown in FIG. 3.

In certain embodiments, outer apertures 132, 134, may extend inwardly toward longitudinal axis 106 from exposed surface 112 to bone-facing surface 114 of bone plate 100, such that bone screws 150 (FIG. 1) located in outer apertures 132, 134, will point toward one another beneath bone-facing surface 114 of bone plate 100. In other embodiments, outer apertures 132, 134, may extend substantially parallel to central apertures 130, or even slightly outwardly from longitudinal axis 106, from exposed surface 112 to bone-facing surface 114 of bone plate 100. With central apertures 130 and outer apertures 132, 134, extending in parallel, bone screws 150 may be able to extend around even a large implant, like hip stem 60, as shown in FIG. 1. Thus, bone plate 100 may be secured in place using bicortical or cancellous bone screws 150 that extend around and beyond hip stem 60.

As shown in FIG. 3, side walls 108, 110, may undulate within periprosthetic zone 120. For example, side walls 108, 110 of bone plate 100 may include concave indentations 140, with adjacent indentations 140 forming apex 142 therebetween. Each indentation 140 may follow an arcuate path between each apex 142, reaching a maximum depth in bone plate 100 at base 144. The undulating pattern may increase in intensity toward proximal end 102 of bone plate 100, with indentations 140 increasing in length and/or depth toward proximal end 102 of bone plate 100.

Along side wall 108 of bone plate 100, indentations 140 may extend between adjacent outer apertures 132, such that bone plate 100 widens enough at apex 142 to accommodate outer apertures 132 but narrows between adjacent outer apertures 132. Similarly, along side wall 110 of bone plate 100, indentations 140 may extend between adjacent outer apertures 134, such that bone plate 100 widens enough at apex 142 to accommodate outer apertures 134 but narrows between adjacent outer apertures 134.

By vertically offsetting outer apertures 132, 134, from central apertures 130, as discussed above, the width W of bone plate 100 may be reduced, because outer apertures 132, 134, may be bordered by at least one indentation on the opposite side wall 108, 110 (e.g., side wall 108, 110, opposite from apex 142). In an exemplary embodiment, the overall width W of bone plate 100 in periprosthetic zone 120, measured between apex 142 on side wall 108 and apex 142 on side wall 110, is about 25 mm. However, at any one point along longitudinal axis 106, such as between apex 142 on side wall 108 and base 144 on side wall 110, the width W of bone plate 100 in periprosthetic zone 120 may be about 3 mm, 4 mm, or 5 mm less, such as about 21 mm. The width W of bone plate 100 within periprosthetic zone 120 may reach a minimum along central apertures 130, because central apertures 130 may be bordered by indentations 140 along both side walls 108, 110. The smooth shape of side walls 108, 110, and the narrow width W of bone plate 100 within periprosthetic zone 120 facilitate smooth insertion of bone plate 100 beneath the muscle tissue of the patient.

According to an exemplary embodiment of the present invention, in a direction perpendicular to longitudinal axis 106, each apex 142 is aligned with an opposing base 144, as shown in FIG. 3. Therefore, when one side wall 108 of bone plate 100 reaches a maximum width at apex 142, the other side wall 110 of bone plate 100 reaches a minimum width at base 144. In this embodiment, indentations 140 on opposing side walls 108, 110, may cooperate to maintain a substantially constant width W of bone plate 100 within periprosthetic zone 120. This simultaneous, opposite behavior of side walls 108, 110, further facilitates smooth insertion of bone plate 100 beneath the muscle tissue of the patient. When bone plate 100 is implanted, side walls 108, 110, will slide across the patient's muscle tissue. As side wall 108 gradually widens toward apex 142, side wall 108 will extend deeper and deeper into the muscle tissue along side wall 108. At the same time, side wall 110 will gradually narrow toward base 144 and gradually free itself from the muscle tissue along side wall 110. Resistance from muscle tissue along side wall 108 may force bone plate 100 back toward the muscle tissue along side wall 110, thereby reducing the risk of shredding the muscle tissue along side wall 108. This cooperation between side walls 108, 110, continues along the length of periprosthetic zone 120.

Like periprosthetic zone 120, non-periprosthetic zone 122 and transition zone 124 of bone plate 100 may include a plurality of central apertures 130 that are generally aligned along longitudinal axis 106 of bone plate 100. However, unlike periprosthetic zone 120, non-periprosthetic zone 122 and transition zone 124 may not require outer apertures 132, 134. For this reason, bone plate 100 may be narrower in non-periprosthetic zone 122 and transition zone 124 than in periprosthetic zone 120, as shown in FIG. 3.

In operation, and as shown in FIGS. 1 and 2, a surgeon may secure bone plate 100 onto the patient's femur 50 using bone screws 150 without interfering with and/or damaging hip stem 60. In proximal end 52 of femur 50 adjacent to hip stem 60, the surgeon may offset bone screws 150 from hip stem 60 by inserting bone screws 150 into outer apertures 132, 134, rather than central apertures 130, in periprosthetic zone 120 of bone plate 100. For example, in the illustrated embodiment of FIG. 1, bone screws 150 may be anteriorly and/or posteriorly offset from hip stem 60. Because bone screws 150 may be entirely offset from hip stem 60, bone plate 100 may be secured in place using bicortical or cancellous bone screws 150, as shown in FIG. 1. Bicortical or cancellous bone screws 150 may strengthen the fixation between femur 50 and bone plate 100, while still avoiding hip stem 60. Rather than avoiding central apertures 130 in periprosthetic zone 120 of bone plate 100, it is also within the scope of the present invention that the surgeon may insert unicortical screws into those central apertures 130 that stop short of hip stem 60. In the distal end (not shown) of femur 50 beneath hip stem 60, the surgeon may insert bicortical, cancellous, or unicortical bone screws 150 centrally into femur 50 by inserting bone screws 150 into central apertures 130 in non-periprosthetic zone 122 and transition zone 124 of bone plate 100. In this distal region of femur 50, the surgeon will not risk interfering with and/or damaging hip stem 60. Suitable cancellous bone screws may be about 4 mm in length, and suitable bicortical bone screws may be about 5 mm in length.

Figure 5:
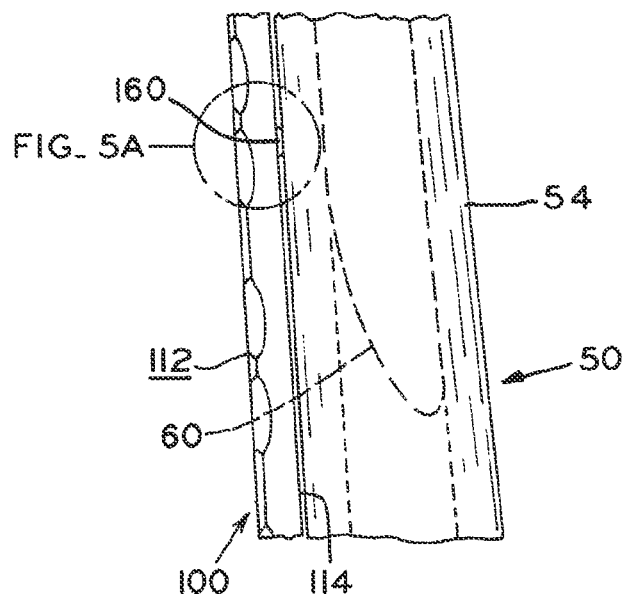
FIG. 5 is an elevational view of a portion of the bone plate of FIG. 1 secured onto the femur, the bone plate spaced apart from the femur with a spacer.
Figure 5A:
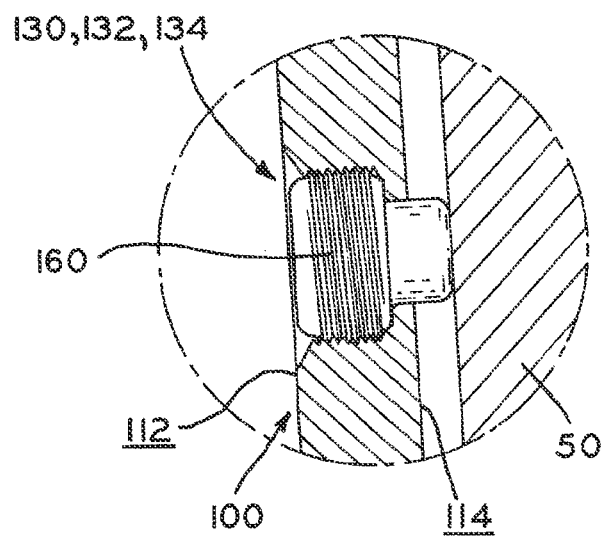
FIG. 5A is a cross-sectional view of the encircled portion of FIG. 5.

According to an exemplary embodiment of the present invention, bone plate 100, and specifically periprosthetic zone 120 of bone plate 100, may be spaced apart from femur 50. For example, as shown in FIGS. 5 and 5A, the surgeon may insert spacers 160 into unoccupied central apertures 130 of bone plate 100 to elevate bone-facing surface 114 of bone plate 100 off of femur 50. Spacers 160 may be provided in various sizes, such as 1 mm, 2 mm, and 3 mm in length, to alter the spacing between bone plate 100 and femur 50. Advantageously, spacing bone plate 100 apart from femur 50 may allow adequate blood flow to the periosteum of femur 50, thereby facilitating healing of femur 50.

According to another exemplary embodiment of the present invention, bone plate 100 may accommodate polyaxial bone screws 150 in central apertures 130, as well as in outer apertures 132, 134. Apertures 130, 132, 134, may be sized to receive bone screws 150 in a perpendicular arrangement, as shown in FIGS. 9 and 9A, or in an angled arrangement, as shown in FIGS. 8 and 8A. In the angled arrangement of FIG. 8, bone screw 150 may be offset up to 15 degrees in any direction from the perpendicular arrangement of FIG. 9. To maintain bone screw 150 in the desired position, the surgeon may insert locking cap 152 into the corresponding aperture 130, 132, 134, and onto bone screw 150. Advantageously, polyaxial bone screws 150 enable the surgeon to manipulate and position bone screws 150 in the desired portion of femur 50 while avoiding hip stem 60 (FIG. 1), if necessary.

As shown in FIGS. 1 and 2, bone plate 100 may include wire apertures 164 that are sized for receipt of cerclage wire 162 therethrough. In operation, before inserting bone screws 150 into femur 50, the surgeon may initially secure bone plate 100 onto femur 50 by wrapping wire 162 through apertures 164 of bone plate 100 and around femur 50. Alternatively, if the surgeon determines that femur 50 is not in the proper condition to receive bone screws 150, the surgeon may secure bone plate 100 onto femur 50 using wire 162 instead of bone screws 150.

Figure 10:
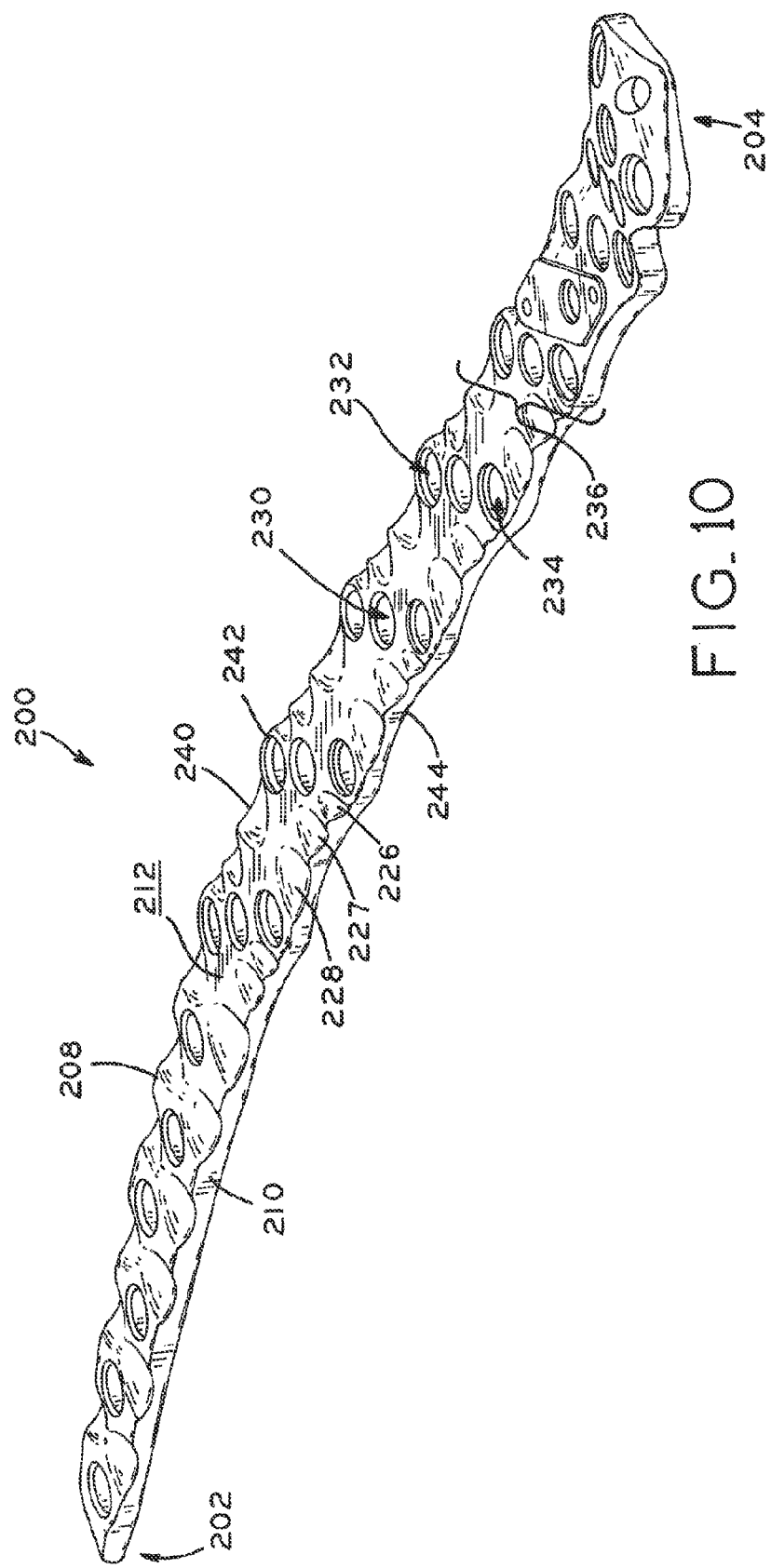
FIG. 10 is a perspective view of another exemplary bone plate of the present invention.

Referring next to FIGS. 10-12, bone plate 200 of the present invention is provided for use on a distal femur (not shown). Bone plate 200 is configured for use on a patient's right leg, although a mirror image plate may be provided for use on a patient's left leg. Bone plate 200 is similar to bone plate 100, with like reference numerals indicating like elements.

Bone plate 200 includes periprosthetic zone 220, non-periprosthetic zone 222, and transition zone 224 located between periprosthetic zone 220 and non-periprosthetic zone 222. As shown in FIG. 11, periprosthetic zone 220 is located near distal end 204 of bone plate 200 and non-periprosthetic zone 222 is located near proximal end 202 of bone plate 200. Bone plate 200 also includes longitudinal axis 206 and side walls 208, 210, that extend from proximal end 202 to distal end 204 of bone plate 100. Rather than being a straight line, longitudinal axis 206 of bone plate 200 may have a slight bend to accommodate the shape of the patient's bone.

In operation, distal end 204 of bone plate 200 is configured to rest against the distal end (not shown) of femur 50, with bone plate 200 extending proximally along shaft 54 of femur 50 and across fracture 56 (FIG. 1). With periprosthetic zone 220 of bone plate 200 located at distal end 204 of bone plate 200, the surgeon may avoid interfering with and/or damaging a prosthetic component implanted in the patient's distal femur, such as a femoral stem of a knee replacement system (not shown).

Bone plate 200 further includes a first, exposed surface 212 and a second, bone-facing surface 214 that span between side walls 208, 210. According to an exemplary embodiment of the present invention, and as shown in FIG. 10, surfaces 212, 214, of bone plate 200 are generally planar to facilitate smooth insertion of the bone plate 200 beneath muscle tissue of the patient. For example, as disclosed in the above-incorporated U.S. patent application Ser. No. 12/683, 962, exposed surface 212 of bone plate 200 may have a central planar region near longitudinal axis 206 in a cross-section perpendicular to longitudinal axis 206, and bone-facing surface 214 of bone plate 200 may have outer planar regions near side walls 208, 210, in the same cross-section perpendicular to longitudinal axis 206. It is within the scope of the present invention that surfaces 212, 214, of bone plate 200 may be contoured to the shape of femur 50 (FIG. 1). For example, as disclosed in the above-incorporated U.S. patent application Ser. No. 12/683,962, bone-facing surface 214 of bone plate 200 may include a concave region between the outer planar regions that is configured to wrap around femur 50.

To accommodate bones of different sizes, bone plate 200 may be provided in various sizes. For example, bone plate 200 may vary in length L along longitudinal axis 206 from approximately 238 mm to approximately 393 mm. According to an exemplary embodiment of the present invention, a set of bone plates 200 may be provided in lengths of 238 mm, 278 mm, 316 mm, 355 mm, and 393 mm, for example.

As shown in FIG. 11, exposed surface 212 of bone plate 200 includes a plurality of concave scallops 226, 227, 228, of various sizes. Scallops 226, 227, 228, are arranged along side walls 208, 210, of bone plate 100 to narrow the thickness T (FIG. 12) of bone plate 200 and to control the mechanical resistance of bone plate 200. For example, bone plate 200 may be configured to bend along large scallops 228 to a greater extent than along small scallops 226. Each scallop 226, 227, 228, may have a maximum depth along its corresponding side wall 208, 210, of bone plate 200, with each scallop 226, 227, 228, gradually decreasing in depth inwardly toward longitudinal axis 206 of bone plate 200, as shown in FIG. 10.

Within periprosthetic zone 220, bone plate 200 includes a plurality of central apertures 230 that are generally aligned along longitudinal axis 206 of bone plate 200, as shown in FIG. 11. Bone plate 200 also includes a plurality of outer apertures 232, 234, positioned alongside central apertures 230.

As shown in FIG. 11, outer apertures 232, 234, are horizontally offset (e.g., medially/laterally offset, anteriorly/posteriorly offset) from central apertures 230. The center of each outer aperture 232, 234, may be horizontally offset from the center of the adjacent central aperture 230 by approximately 5 mm, 6 mm, 7 mm, 8 mm, 9 mm, 10 mm, or more. In an exemplary embodiment, the center of each outer aperture 232, 234, is horizontally offset from the center of the adjacent central aperture 230 by approximately 7.5 mm, such that the centers of outer apertures 232, 234, are horizontally offset from one another by approximately 13 mm. In certain embodiments, outer apertures 232 may be arranged in a first row that is generally parallel to central apertures 230, and outer apertures 234 may be arranged in a second row that is also generally parallel to central apertures 230.

Also, as shown in FIG. 11, outer apertures 232, 234 are vertically offset (e.g., proximally/distally offset) from central apertures 230 and each other. The center of each outer aperture 232, 234, may be vertically offset from the center of the adjacent central aperture 230 by approximately 5 mm, 6 mm, 7 mm, 8 mm, 9 mm, 10 mm, or more. By vertically offsetting outer apertures 232, 234, from central apertures 230, the width W of bone plate 200 may be reduced. If central apertures 230 and outer apertures 232, 234, were all aligned in a direction perpendicular to longitudinal axis 206, on the other hand, bone plate 200 would have to be sufficiently wide in this perpendicular direction to accommodate all three apertures 230, 232, 234.

According to an exemplary embodiment of the present invention, three apertures 230, 232, 234, may be organized in a subset 236 that extends diagonally across bone plate 200, as shown in FIG. 11. Bone plate 200 may include a plurality of spaced-apart subsets 236 across its length. In certain embodiments, the entire subset 236 of apertures 230, 232, 234, is vertically offset (e.g., proximally/distally offset) from the adjacent subset 236. Large scallops 228 may extend between adjacent subsets 236, with small scallops 226 and medium scallops 227 extending into each subset 236, as shown in FIG. 11.

In certain embodiments, outer apertures 232, 234, may extend inwardly toward longitudinal axis 206 from exposed surface 212 to bone-facing surface 214 of bone plate 200, such that bone screws 150 (FIG. 1) located in outer apertures 232, 234, will point toward one another beneath bone-facing surface 214 of bone plate 200. In other embodiments, outer apertures 232, 234, may extend substantially parallel to central apertures 230, or even slightly outwardly from longitudinal axis 206, from exposed surface 212 to bone-facing surface 214 of bone plate 200. With central apertures 230 and outer apertures 232, 234, extending in parallel, bone screws 150 may be able to extend around and beyond the knee implant. Thus, bone plate 200 may be secured in place using bicortical or cancellous bone screws 150, while still avoiding the knee implant.

As shown in FIG. 11, side walls 208, 210, may undulate within periprosthetic zone 220. For example, side walls 208, 210 of bone plate 200 may include concave indentations 240, with adjacent indentations 240 forming apex 242 therebetween. Each indentation 240 may follow an arcuate path between each apex 242, reaching a maximum depth in bone plate 200 at base 244. The undulating pattern may increase in intensity toward proximal end 202 of bone plate 200, with indentations 240 increasing in length and/or depth toward proximal end 202 of bone plate 200.

Along side wall 208 of bone plate 200, indentations 240 may extend between adjacent outer apertures 232, such that bone plate 200 widens enough at apex 242 to accommodate outer apertures 232 but narrows between adjacent outer apertures 232. Similarly, along side wall 210 of bone plate 200, indentations 240 may extend between adjacent outer apertures 234, such that bone plate 200 widens enough at apex 242 to accommodate outer apertures 234 but narrows between adjacent outer apertures 234.

By vertically offsetting outer apertures 232, 234, from central apertures 230, as discussed above, the width W of bone plate 200 may be reduced, because outer apertures 232, 234, may be bordered by at least one indentation on the opposite side wall 208, 210 (e.g., side wall 208, 210, opposite from apex 242). In an exemplary embodiment, the overall width W of bone plate 200 in periprosthetic zone 220, measured between apex 242 on side wall 208 and apex 242 on side wall 210, is about 28 mm. However, at any one point along longitudinal axis 206, such as between apex 242 on side wall 208 and base 244 on side wall 210, the width W of bone plate 200 in periprosthetic zone 220 may be about 3 mm, 4 mm, or 5 mm less, such as about 23 mm. The width W of bone plate 200 within periprosthetic zone 220 may reach a minimum along central apertures 230, because central apertures 230 may be bordered by indentations 240 along both side walls 208, 210. The smooth shape of side walls 208, 210, and the narrow width W of bone plate 200 within periprosthetic zone 220 facilitate smooth insertion of bone plate 200 beneath the muscle tissue of the patient.

According to an exemplary embodiment of the present invention, in a direction perpendicular to longitudinal axis 206, each apex 242 is aligned with an opposing base 244, as shown in FIG. 11. Therefore, when one side wall 208 of bone plate 200 reaches a maximum width at apex 242, the other side wall 210 of bone plate 200 reaches a minimum width at base 244. In this embodiment, indentations 240 on opposing side walls 208, 210, may cooperate to maintain a substantially constant width W of bone plate 200 within periprosthetic zone 220. This simultaneous, opposite behavior of side walls 208, 210, further facilitates smooth insertion of bone plate 200 beneath the muscle tissue of the patient, as discussed above with respect to bone plate 100 (FIGS. 2-4).

Like periprosthetic zone 220, non-periprosthetic zone 222 and transition zone 224 of bone plate 200 may include a plurality of central apertures 230 that are generally aligned along longitudinal axis 206 of bone plate 200. However, unlike periprosthetic zone 220, non-periprosthetic zone 222 and transition zone 224 may not require outer apertures 232, 234. For this reason, bone plate 200 may be narrower in non-periprosthetic zone 222 and transition zone 224 than in periprosthetic zone 220, as shown in FIG. 11.

In operation, and as shown in FIG. 11, a surgeon may secure bone plate 200 onto the patient's distal femur (not shown) using bone screws 150 (FIG. 1) without interfering with and/or damaging a prosthetic component implanted in the patient's distal femur, such as a femoral stem of a knee replacement system (not shown). In the distal end of femur 50 adjacent to the knee implant, the surgeon may offset bone screws 150 from the knee implant by inserting bone screws 150 into outer apertures 232, 234, rather than central apertures 230, in periprosthetic zone 220 of bone plate 200. Because bone screws 150 may be entirely offset from the knee implant, bone plate 200 may be secured in place using bicortical or cancellous bone screws 150. Bicortical or cancellous bone screws 150 may strengthen the fixation between femur 50 and bone plate 200, while still avoiding the knee implant. Rather than avoiding central apertures 230 in periprosthetic zone 220 of bone plate 200, it is also within the scope of the present invention that the surgeon may insert unicortical screws into those central apertures 230 that stop short of the knee implant. Toward proximal end 52 of femur 50 above the knee implant, the surgeon may insert bicortical, cancellous, or unicortical bone screws 150 centrally into femur 50 by inserting bone screws 150 into central apertures 230 in non-periprosthetic zone 222 and transition zone 224 of bone plate 200. In this proximal region of femur 50, the surgeon will not risk interfering with and/or damaging the knee implant.

Like bone plate 100 (FIGS. 2-4), bone plate 200 may be configured to receive spacers 160 (FIGS. 5 and 5A), polyaxial bone screws 150 (FIGS. 6-9), and/or cerclage wire 162 (FIG. 1) for securing bone plate 200 onto femur 50.

Referring next to FIGS. 13-16, bone plates 300, 400, 500, of the present invention are provided for use on proximal end 52 of femur 50 (FIG. 1), much like bone plate 100 described above with reference to FIGS. 2-4. Bone plates 300, 400, 500, are similar to bone plate 100, with like reference numerals indicating like elements.

Each bone plate 300, 400, 500, includes periprosthetic zone 320, 420, 520, non-periprosthetic zone 322, 422, 522, and transition zone 324, 424, 524, located between periprosthetic zone 320, 420, 520, and non-periprosthetic zone 322, 422, 522. Unlike bone plate 100 (FIG. 2), each bone plate 300, 400, 500, further includes trochanteric zone 370, 470, 570, that extends proximally beyond periprosthetic zone 320, 420, 520. In operation, the surgeon is able to secure trochanteric zone 370, 470, 570, of the corresponding bone plate 300, 400, 500, onto greater trochanter 58 of femur 50 (FIG. 1) for added stability. In the illustrated embodiments of FIGS. 13-16, each bone plate 300, 400, 500, is ring-shaped in the corresponding trochanteric zone 370, 470, 570, such that bone plate 300, 400, 500, is able to wrap around greater trochanter 58 of femur 50 with bone of femur 50 protruding therethrough, as necessary.

As shown in FIGS. 13 and 14, each trochanteric zone 370, 470, may be integrally formed with periprosthetic zone 320, 420, of the corresponding bone plate 300, 400. Alternatively, and as shown in FIGS. 15 and 16, trochanteric zone 570 may be removably coupled to periprosthetic zone 520 of the corresponding bone plate 500 using suitable fasteners, such as screws 572. In this modular embodiment of FIGS. 15 and 16, bone plate 500 may be used with or without trochanteric zone 570 attached thereto.

Additional information regarding the bone plates of the present invention may be found in the above-incorporated U.S. patent application Ser. No. 12/683,962.

Additional information regarding methods and tools for implanting the bone plates of the present invention may be found in U.S. patent application Ser. No. 12/683,953, entitled "Bone Plate Fixation System," filed Jan. 7, 2010, the disclosure of which is hereby expressly incorporated by reference herein in its entirety.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone plate for use with a bone having a periprosthetic fracture, the bone plate having a longitudinal axis that extends from a first end to a second end of the bone plate, the bone plate comprising:
   a bottom surface configured to face the bone;
   a top surface opposite the bottom surface;
   a first side wall and a second side wall joining the top and bottom surfaces; and
   a periprosthetic zone located toward the first end of the bone plate, the periprosthetic zone including:
      a plurality of spaced-apart aperture subsets positioned along the length of the periprosthetic zone of the bone plate, wherein each subset of the plurality of spaced-apart aperture subsets includes three apertures extending diagonally across the bone plate relative to the longitudinal axis; and
      a plurality of apexes formed between adjacent indentations along the first and second side walls, wherein the plurality of apexes and the indentations along the first and second side walls cooperate to maintain a substantially constant width at every point along a portion of the longitudinal axis of the bone plate extending between at least two apexes along the first wall of two adjacent spaced-apart aperture subsets within the periprosthetic zone.

2. The bone plate of claim 1, wherein each subset of the plurality of spaced-apart aperture subsets includes a central aperture, a first outer aperture, and a second outer aperture.

3. The bone plate of claim 2, wherein the first outer aperture is located on a first side of the central aperture and adjacent to a first apex along the first side wall and the second outer aperture is located on a second side of the central aperture and adjacent to a second apex along the second side wall, the second side of the central aperture directly opposite the first side of the central aperture.

4. The bone plate of claim 2, wherein the first outer aperture and the second outer aperture of each subset is sized to receive a polyaxial bone screw, the polyaxial bone screw adjustable between a collinear arrangement and an angled arrangement relative to an axis of the first outer aperture and the second outer aperture.

5. The bone plate of claim 1, further including a non-periprosthetic zone located toward the second end of the bone plate and a transition zone located between the non-periprosthetic zone and the periprosthetic zone, wherein the transition zone and the non-periprosthetic zone include a plurality of central apertures that extend along the longitudinal axis.

6. The bone plate of claim 1, further including a plurality of scallops that extend into the bone plate, wherein at least a first scallop of the plurality of scallops is positioned between two adjacent spaced-apart aperture subsets along the first side wall of the bone plate and at least a second scallop of the plurality of scallops is positioned between the two adjacent spaced-apart aperture subsets along the second side wall of the bone plate.

7. A bone plate for use with a bone having a periprosthetic fracture, the bone plate having a longitudinal axis that extends from a first end to a second end of the bone plate, the bone plate comprising:
   a bottom surface configured to face the bone;
   a top surface opposite the bottom surface;
   a first side wall and a second side wall joining the top and bottom surfaces;
   a periprosthetic zone located toward the first end of the bone plate, the periprosthetic zone including:
      a plurality of central apertures that extend along the longitudinal axis;
   a plurality of outer apertures, each outer aperture of the plurality of outer apertures vertically and horizontally offset from a corresponding central aperture of the plurality of central apertures; and
   a plurality of indentations in the first and second side walls, each indentation extending longitudinally between adjacent outer apertures, wherein the indentations on opposing side walls cooperate to maintain a substantially constant width along a portion of the bone plate within the periprosthetic zone; and
   a non-periprosthetic zone located toward the second end of the bone plate, the non-periprosthetic zone including only central apertures extending along the longitudinal axis.

8. The bone plate of claim 7, further including a transition zone located between the non-periprosthetic zone and the periprosthetic zone.

9. The bone plate of claim 8, wherein the transition zone and the non-periprosthetic zone include a plurality of central apertures that extend along the longitudinal axis.

10. The bone plate of claim 8, wherein the transition zone contains only central apertures.

11. The bone plate of claim 8, wherein the first and second side walls along the transition zone and the non-periprosthetic zone have a substantially flat surface.

12. The bone plate of claim 8, wherein a first width of the bone plate along the periprosthetic zone is greater than a second width of the bone plate along the transition zone and a third width of the bone plate along the non-periprosthetic zone.

13. The bone plate of claim 12, wherein the second width of the bone plate along the transition zone is greater than the third width of the bone plate along the non-periprosthetic zone.

14. The bone plate of claim 8, wherein a first thickness of the bone plate along the transition zone is greater than a second thickness of the bone plate along the periprosthetic zone and a third thickness of the bone plate along the non-periprosthetic zone.

15. The bone plate of claim 7, wherein adjacent indentations along the first and second side walls form an apex therebetween, and wherein each indentation extends inwardly toward the longitudinal axis of the bone plate until reaching a maximum depth at a base.

16. The bone plate of claim 15, wherein a first base on a first side of the bone plate aligns with a first apex on an opposing second side of the bone plate in a direction perpendicular to the longitudinal axis of the bone plate.

17. The bone plate of claim 7, wherein each of the plurality of outer apertures is sized to receive a polyaxial bone screw, the polyaxial bone screw adjustable between a collinear arrangement and an angled arrangement relative to an axis of the plurality of outer apertures.

18. A bone plate for use with a bone having a periprosthetic fracture, the bone plate having a longitudinal axis that extends from a first end to a second end of the bone plate, the bone plate comprising:
   a bottom surface configured to face the bone;
   a top surface opposite the bottom surface;
   a first side wall and a second side wall joining the top and bottom surfaces; and
   a periprosthetic zone located toward the first end of the bone plate, the periprosthetic zone including:
      a plurality of spaced-apart aperture subsets positioned along the length of the periprosthetic zone of the bone plate, wherein each subset of the plurality of spaced-apart aperture subsets includes three apertures extending diagonally across the bone plate relative to the longitudinal axis; and
      a plurality of apexes formed between adjacent indentations along the first and second side walls, wherein the first and second side walls move a distance from the longitudinal axis along at least a portion of the perirposthetic zone such that as the first wall side narrows inwardly toward the longitudinal axis the second side wall widens outwardly from the longitudinal axis in a simultaneous opposite behavior.

* * * * *